(12) United States Patent
Ma et al.

(10) Patent No.: US 7,989,212 B2
(45) Date of Patent: Aug. 2, 2011

(54) DETECTION OF BLOOD PLASMA SCHIZADRIN B OF DISSIPATING BLOOD STASIS BOTANICAL

(75) Inventors: Yueming Ma, Shanghai (CN); Rong Shi, Shanghai (CN); Yongyu Zhang, Shanghai (CN)

(73) Assignee: Shanghai Sundise, Changning District, Shanghai (CN)

( * ) Notice: Subject to any disclaimer, the term of this patent is extended or adjusted under 35 U.S.C. 154(b) by 0 days.

(21) Appl. No.: 12/451,141

(22) PCT Filed: Apr. 28, 2008

(86) PCT No.: PCT/CN2008/000865
§ 371 (c)(1),
(2), (4) Date: Oct. 27, 2009

(87) PCT Pub. No.: WO2008/131647
PCT Pub. Date: Nov. 6, 2008

(65) Prior Publication Data
US 2010/0093103 A1    Apr. 15, 2010

(30) Foreign Application Priority Data
Apr. 27, 2007   (CN) .......................... 2007 1 0040140

(51) Int. Cl.
*G01N 33/00*   (2006.01)
(52) U.S. Cl. ........................................ 436/131; 436/173
(58) Field of Classification Search .................. 436/131
See application file for complete search history.

(56) References Cited

U.S. PATENT DOCUMENTS
2007/0160626 A1   7/2007  Zhang et al.

| | | |
|---|---|---|
| 2010/0093099 A1 | 4/2010 | Ma et al. |
| 2010/0093103 A1 | 4/2010 | Ma et al. |
| 2010/0119541 A1 | 5/2010 | Xu et al. |

FOREIGN PATENT DOCUMENTS

| | | |
|---|---|---|
| CN | 1243743 | 2/2000 |
| CN | 99113887.2 | 8/2001 |
| CN | 1472532 | 2/2004 |
| CN | 1669573 | 9/2005 |
| CN | 02136002.2 | 9/2005 |

(Continued)

OTHER PUBLICATIONS

Dou, et al, "Analysis of Lignans in serum of rats after oral administration of compound Wurenchun capsules by UPLC-MS/MS", Chinese Traditional Patent Medicine, Apr. 2007, vol. 29(4), pp. 550-555.

(Continued)

*Primary Examiner* — Yelena G Gakh
(74) *Attorney, Agent, or Firm* — Yunling Ren

(57) ABSTRACT

A detection method of blood plasma schizadrin B of dissipating blood stasis botanical is disclosed. The method includes: (1) extracting schizadrin B from plasma of mammalian administered dissipating blood stasis botanical by ethyl acetate with the volume ratio 1:4, whirling 3-5 mins, centrifugating at 9600 rpm for 10 mins, drying and enriching the upper layer at 25-30° C., and redissolving with mobile phase; (2) UPLC/MS measuring: UPLC condition: chromatographic column: Acquity UPLC BEH $C_{18}$, 2.1'100 mm, mobile phase A: water-acetonitrile-formic acid 95:5:0.1 v/v/v, mobile phase B: acetonitrile-formic acid 100:0.1 v/v; MS condition: electric spraying ion source (ESI), detecting with positive ion mode, scanning at the range of m/z 150-1200. The method can be used for pharmacokinetics study of schizadrin B in dissipating blood stasis botanical.

2 Claims, 1 Drawing Sheet

A. Schizadrin B; B. strengthening body resistance and dissipating blood stasis; C. blank plasma; D. Plasma of mammals taken 0.5 hours after drenched with strengthening body resistance and dissipating blood stasis botanical

FOREIGN PATENT DOCUMENTS

| | | |
|---|---|---|
| CN | 1839996 | 10/2006 |
| CN | 1925864 | 3/2007 |
| CN | 1959409 | 5/2007 |
| CN | 101042380 | 9/2007 |
| CN | 2007100401416 | 9/2007 |
| CN | 101078712 | 11/2007 |
| CN | 200710040331.8 | 12/2009 |
| CN | 200510028951.0 | 3/2010 |
| JP | 1165583 | 6/1989 |
| KR | 20060038027 | 5/2006 |
| WO | 01/41778 | 6/2001 |
| WO | 2004/014409 | 2/2004 |
| WO | 2007/020382 | 2/2007 |

OTHER PUBLICATIONS

Yan, et al, "Pharmacokinetics study of schisandrin in Shengmai granule", TraiditonalChinese Drug Research & Clinical Pharmacology, Jan. 2006, vol. 17(1), pp. 36-39.

Liao, et al, "The study in situ on rat intestinal absorption of the active components in GuizhiFuling capsule", Chin. J. Nat. Med., Sep. 2005, vol. 3(5), pp. 303-307.

Xie, et al, "Determinination of anthraquinones and amygdalin in "Taohe Chengqi Decoction", by HPLC", SH. J. TCM, Jul. 2006, vol. 40(7), pp. 73-76.

Pan, et al, "Pharmacokinetics and bioavailability study of danshensu in rat", China Journal of Chinese Materia Medica, Jan. 2008, vol. 33(2), pp. 146-149.

Chen et al, "LC-MS/MS-based measurement of danshen phenolic acids in plasma", Chin. J. Clin Pharmacol Ther, Jul. 2007, vol. 12(7), pp. 748-755.

Tan, et al, "Research Concerning Influence of "Fuzheng Huayu Decoction" on Hepatocellular Apoptosis in Rats with DMN Liver Fibrosis", A Collection of Papers of the 12th National Symposium on Liver Disease with Chinese Integrative Medicine, 2003, pp. 219-223.

She, et al, "Clinical Research of Ganping Capsule Treating Liver Fibrosis in Patients with Chronic Hepatitis B", Chinese Heptology, Dec. 2002, vol. 7(4), pp. 254-255.

Lou, et al, "Comparison of schisandrin and schisandrin B in rat serum and plasma after ig Compound Wurenchun Capsules", Chinese Traditional and Herbal Drugs, vol. 37(10), Oct. 2006; pp. 1486-1489.

Xu, et al, "Determination of schizandrin in rat plasma by high-performance liquid chromatography—mass spectrometry and its application in rate pharmacokinetic studies", Journal of Chromatography B, vol. 828, 2005, pp. 55-61.

He, et al, "Analysis of lignan constituents from Schisandra chinensis by liquid chromatography—electrospray mass spectrometry", Journal of Chromatography A, vol. 757, 1997, pp. 81-87.

Database Biosis (Online) Biosciences Information Service, Philadelphia, PA, Feb. 2000; Baek Nam-In, et al, "Isolation of anticonvulsant compounds from the fruits of Schizandra chinensis Baili" Database accession No. PREV200000198785.

Churchwell, et al, "Improving LC-MS sensitivity through increases in chromatographic performance: Comparisons of UPLC-ES/MS/MS to HPLC-ES/MS/MS", Journal of Chromatography B, vol. 825, 2005, pp. 134-143.

Park, et al, "HPLC Assay and Bioequivalence Evlaution of Biphenyl Dimethyl Dicarboxylate (DDB) Products", J. Liq. Chrom, & Rel. Technol., vol. 21(12), 1998, pp. 1833-1843.

Zhao, et al, "HPLC with Column Switching Coupled to APCI-MS for Pharmacokinetic Study of Amygdalin in Rabbit Plasma", Chromatographia, vol. 65, 2007, pp. 149-153.

Kang, et al, "Micellar electrokinetic chromatography for the analysis of D-amygdalin and its epimer in apricot kernal", Journal of Chromatography A, vol. 866, 2000, pp. 253-259.

Liu, et al, "Effect of Fuzheng Huayu formula and its actions against liver fibrosis", Chinese Medicine, vol. 4(12), 2009, pp. 1-11.

Wang, et al, "Fuzheng Huayu recipe and vitamin E reverse renal interstitial fibrosis through counteracting TGF-B1-induced epithelial-to-mesenchymal transition", Journal of Ethnopharmacology, vol. 127, 2010, pp. 631-640.

Office Action dated Feb. 12, 2010 Issued by the State Intellectual Property Office of the People's Republic of China regarding Application No. 2007100403322.

U.S. Appl. No. 12/451,148, filed Oct. 27, 2009.

European Search Report regarding EP Application No. 08748426.7.

European Search Report regarding EP Application No. 08748424.2.

A. Schizadrin B; B. strengthening body resistance and dissipating blood stasis; C. blank plasma; D. Plasma of mammals taken 0.5 hours after drenched with strengthening body resistance and dissipating blood stasis botanical

DETECTION OF BLOOD PLASMA SCHIZADRIN B OF DISSIPATING BLOOD STASIS BOTANICAL

CROSS REFERENCE TO RELATED APPLICATIONS

The present application is a 35 U.S.C. §371 national stage filing of International Patent Application No. PCT/CN2008/000865, filed Apr. 28, 2008, and through which priority is claimed to Chinese Patent Application No. 200710040140.1, filed Apr. 27, 2007, the disclosures of which are incorporated herein by reference in their entireties.

TECHNICAL FIELD

The invention belongs to the field of pharmacokinetics, particularly involves a detection method of blood plasma schizadrin B of strengthening body resistance and dissipating blood stasis botanical (vegetable).

BACKGROUND ART

Strengthening body resistance and dissipating blood stasis botanical are composed of compound prescriptions including salvia miltiorrhiza, peach kernel, *Schisandra chinens* etc., which have the effect of curing liver, lung and kidney fibrosis; however, due to lack of pharmacokinetics research has been carried out on the strengthening body resistance and dissipating blood stasis botanical, so it is not clear about the effective ingredients in vivo, and it is difficult to provide a basis for quality control and guiding clinical rational administration, thus hinder those drugs from entering the international market.

So far, no pharmacokinetics research report on the strengthening body resistance and dissipating blood stasis botanical has been found, and there has not any detection method of schizadrin B of the compound prescription in biological samples (including blood plasma).

CONTENTS OF THE INVENTION

The technical matters aim to be resolved by this invention is to provide a detection method of blood plasma schizadrin B of strengthening body resistance and dissipating blood stasis botanical (vegetable), and the method is used for pharmacokinetics research, and clarifying the pharmacokinetics rules of the blood plasma schizadrin B of strengthening body resistance and dissipating blood stasis botanical (vegetable).

The technical problems solved by the invention are achieved through the following technical solutions:

Detection method of blood plasma schizadrin B of strengthening body resistance and dissipating blood stasis botanical includes the following steps:

(1) Pretreatment of mammalian plasma samples
 a. Mammal plasma containing drugs after being administered the strengthening body resistance and dissipating blood stasis botanical was extracted with ethyl acetate at the volume ratio of 1:4, whirling for 3 to 5 min, then centrifuging at 9600 rpm for 10 min; and drying and enriching the supernatant under the condition of 25 to 30° C.;
 b. Redissolve eluent with mobile phase and then analyze it with UPLC/MS;
(2) UPLC/MS detection UPLC condition: chromatographic column: ACQUITY UPLC BEH C18 (a type of chromatographic column), 2.1×100 mm, mobile phase A: Water-Acetonitrile-Formic acid 95:5:0.1 v/v/v, mobile phase B: Acetonitrile-Formic acid 100:0.1 v/v; MS condition: electrospray ionization (ESI) ion source, detection with positive ion mode, scanning at the range of m/z 150 to 1200.

The described step (2) detects with the positive ion mode; the desolvation gas flow is 440 L/h, the desolvation gas temperature is 300° C., the cone gas flow is 50 L/h, the ion source temperature is 100° C., the spray capillary voltage is 3800 V, the sampling cone voltage is 30V, the extracting cone voltage is 2.00 V, the lens voltage is 0.1 V, and the mass scanning at the range of m/z 150 to 1200.

In the process of the liquid-liquid extraction in this invention, the detected components are distributed in two solvents which are immiscible, select appropriate organic solvents and appropriate proportion, can extract the non-polar components dissolved in the blood plasma entering the organic phase, and then the draining and enriching the organic phase; a UPLC system is used to separate analyte with other components, and finally detected with a mass spectrometric detector.

The ethyl acetate liquid-liquid extraction method adopted by the invention can extract the schizadrin B in the blood plasma, combined with using a UPLC/MS system to detect, markedly improve the resolutions of schizadrin B among other ingredients in the samples, and the analysis method is more sensitive and faster, to facilitate detection of the plasma concentration of the schizadrin B in pharmacokinetic research.

MODE OF CARRYING OUT THE INVENTION

Figure 1:
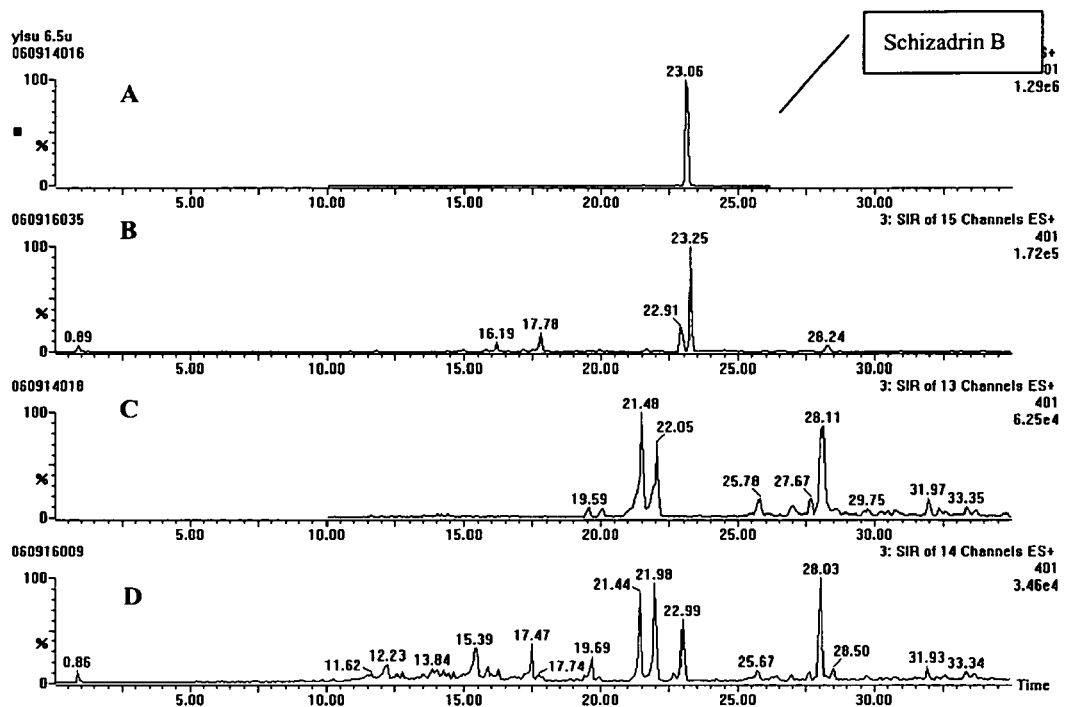
FIG. 1. UPLA-MS Chromatogram of rat's blood plasma Schizandrin B 0.5 hours after being administered with Strengthening Body Resistance and Dissipating Blood Stasis Botanical.

Combined with the specific embodiments, further elaboration of this invention is given below. It should be understood that these embodiments are only for description of the present invention but not for the use of limiting the scope of the present invention. It should also be understood that, after reading the contents taught in this invention, technicians in this field can make various changes or modifications to this invention, these equivalent forms are all included in the scope defined by the claims attached to this application.

Embodiment 1

A detection method of blood plasma schizadrin B of strengthening body resistance and dissipating blood stasis botanical includes:

1. Mammal plasma containing drugs after being administered the strengthening body resistance and dissipating blood stasis botanical was extracted with ethyl acetate with the volume ratio of 1:4, whirling for 3 min, then centrifugating at 9600 rpm for 10 min, and drying and enriching the supernatant under the condition of 25 to 30° C., redissolving the eluent with mobile phase and then analyzing it with UPLC/MS.

2. UPLC/MS detecting method: the analysis conditions of the UPLC/MS method adopted in this invention: chromatographic column: ACQUITY UPLC BEH C18 (a type of chromatographic column), 2.1×100 mm, mobile phase A: Water- Acetonitrile-Formic acid 95:5:0.1 v/v/v, mobile phase B: Acetonitrile-Formic acid 100:0.1 v/v, eluting in accordance with the following gradient:

| Time (min) | Flow Rate (ml/min) | % A | % B |
|---|---|---|---|
| 0 | 0.300 | 100 | 0 |
| 5.00 | 0.300 | 85.0 | 15.0 |
| 10.00 | 0.300 | 70.0 | 30.0 |
| 20.00 | 0.300 | 40.0 | 60.0 |
| 30.00 | 0.300 | 20.0 | 80.0 |
| 35.00 | 0.300 | 20.0 | 80.0 |
| 35.01 | 0.300 | 100.0 | 0.0 |
| 38.00 | 0.300 | 100.0 | 0.0 |

MS conditions: electrospray ionization (ESI) ion source, detecting with positive ion mode; the desolvation gas flow is 440 L/h, the desolvation temperature is 300° C., the cone gas flow is 50 L/h, the ion source temperature is 100° C., the spray capillary voltage is 3800 V, the sampling cone voltage is 30V, the extracting cone voltage is 2.00 V, the lens voltage is 0.1 V, and the mass scanning at the range of m/z 150 to 1200.

Detection results: Schizadrin B can be detected in the plasma of mammals after drenched with strengthening body resistance and dissipating blood stasis botanical (see FIG. 1).

The invention claimed is:

1. A method for detecting the presence of schizandrin B in the blood plasma of an animal after administering the botanical extract composition Strengthening Body Resistance and Dissipating Blood Stasis Botanical to said animal, comprising the steps of:
   a. collecting the blood plasma from said animal 0.5 hours after administration of Strengthening Body Resistance and Dissipating Blood Stasis Botanical to said animal;
   b. extracting said blood plasma with ethyl acetate in a blood plasma to ethyl acetate ratio of 1:4 (v/v) for 3 minutes;
   c. centrifugating the product resulting from step b at 9600 rpm for 10 minutes;
   d. collecting the supernatant after said centrifugation and drying said supernatant at 25-30° C. to produce a dried supernatant;
   e. redissolving said dried supernatant in a mixture of water-acetonitrile-formic acid at a ratio of water:acetonitrile:formic acid equals to 95:5:0.1 (v/v/v) to form a blood plasma solution;
   f. applying said blood plasma solution to a liquid chromatography column having a size of 2.1×100 mm, wherein the chromatography is performed having conditions including a mobile phase A and a mobile phase B, said mobile phase A is the mixture of water-acetonitrile-formic acid in step e and said mobile phase B is a mixture of acetonitrile-formic acid in a ratio of acetonitrile:formic acid equals to 100:1 (v/v); and
   g. detecting the presence of schizandrin B with mass scan at a range of m/z 150-1200, using an electrospray ionization (ESI) with a positive ion mode.

2. The method in claim 1, wherein said detection of the presence of schizandrin B in step g with a positive ion mode, wherein the desolvation gas flow being 440 L/h, the desolvation gas temperature being 300° C., the cone gas flow being 50 L/h, the ion source temperature being 100° C., the spray capillary voltage being 3800 V, the sampling cone voltage being 30V, the extracting cone voltage being 2.00 V, and the lens voltage being 0.1 V.

* * * * *